United States Patent [19]

Byrne

[11] Patent Number: 5,307,790
[45] Date of Patent: May 3, 1994

[54] BRACELET RETRACTOR ASSEMBLY

[75] Inventor: Donny M. Byrne, Conroe, Tex.

[73] Assignee: Surigcal Innovations I, L.P., Conroe, Tex.

[21] Appl. No.: 944,097

[22] Filed: Sep. 11, 1992

[51] Int. Cl.$^5$ ............................................. A61B 17/02
[52] U.S. Cl. ..................................... 128/20; 128/17; 24/20 R
[58] Field of Search .................. 128/20, 3, 12-14, 128/17-19; 24/16 R, 20 R, 23 W; 606/191, 1

[56] References Cited

U.S. PATENT DOCUMENTS

| Re. 32,021 | 11/1985 | Scott, Jr. .......................... | 128/20 |
| 955,006 | 4/1910 | Sparks . | |
| 2,438,646 | 3/1948 | Pulliam ............................. | 128/20 |
| 2,612,891 | 10/1952 | Smith ................................. | 128/20 |
| 2,695,607 | 11/1954 | Hipps et al. ...................... | 128/20 |
| 3,364,919 | 1/1968 | Hunnicutt ......................... | 128/20 |
| 3,762,401 | 10/1973 | Tupper ............................... | 128/20 |
| 3,916,879 | 11/1975 | Cotten ................................ | 128/12 |
| 3,938,508 | 2/1976 | Buckner ............................ | 128/12 |
| 4,418,448 | 12/1983 | Sauer ........................... | 24/20 TT |
| 4,627,421 | 12/1986 | Symbas et al. .................. | 128/20 |
| 5,052,373 | 10/1991 | Michelson ........................ | 128/20 |

FOREIGN PATENT DOCUMENTS

| 690530 | 2/1930 | France . | |
| 410081 | 1/1945 | Italy ................................... | 128/12 |

| 1360706 | 12/1987 | U.S.S.R. ...................... | A61B 17/02 |

OTHER PUBLICATIONS

Murray-Baumgartner Surgical Instruments Catalog, p. 113, Dec. 26, 1934, "Standard Surgical Instruments".

*Primary Examiner*—Richard J. Apley
*Assistant Examiner*—Donna L. Maraglio
*Attorney, Agent, or Firm*—Harrison & Egbert

[57] ABSTRACT

A retractor instrument for opening a surgical incision on a human limb having a first tissue holder for grasping an edge of the incision, a second tissue holder for grasping another edge of the incision, a band extending from the first tissue holder to the second tissue holder in a generally circular configuration around the limb away from the incision, and an adjustor connected to the band so as to vary a distance between the first and second tissue holders. The band includes a first band member connected to the first tissue holder and a second band member connected to the second tissue holder. The adjustor is a clamp which is suitable for engaging grooves formed in the first band member. The tissue holders are rake members having a plurality of prongs extending therefrom. The rake members are pivotally connected to the ends of the bands. The first band member and the second band member are arranged in overlapping configuration.

13 Claims, 4 Drawing Sheets

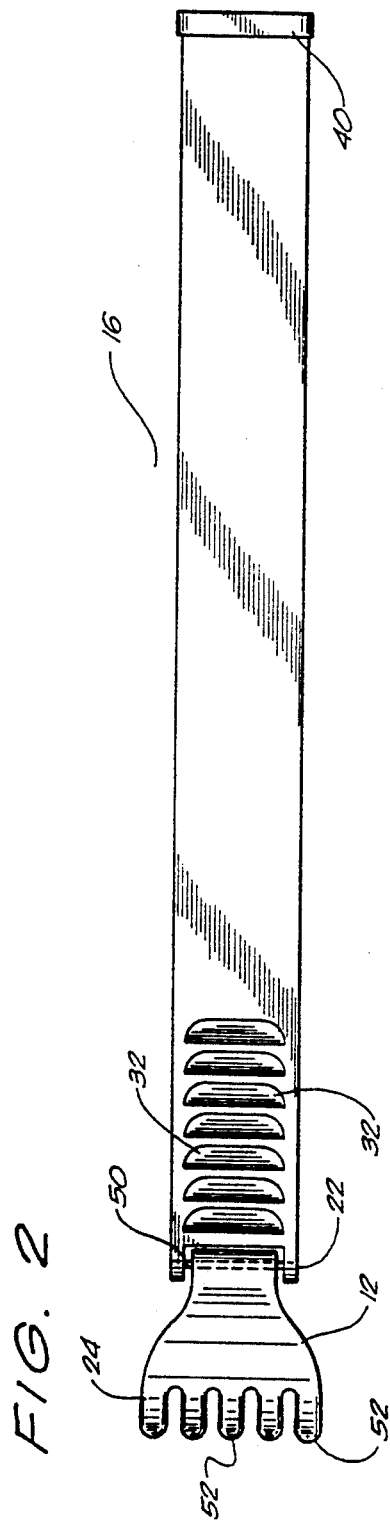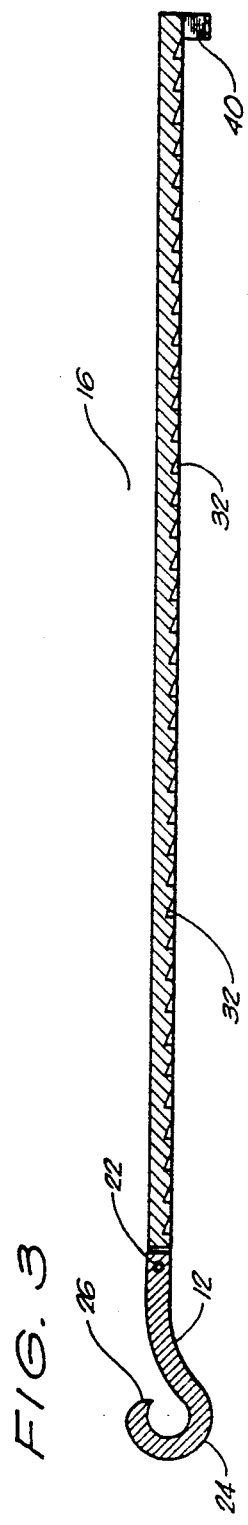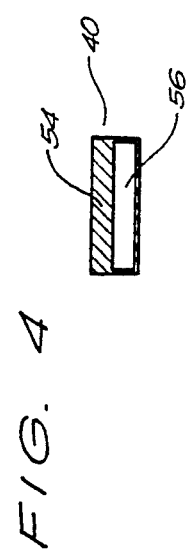

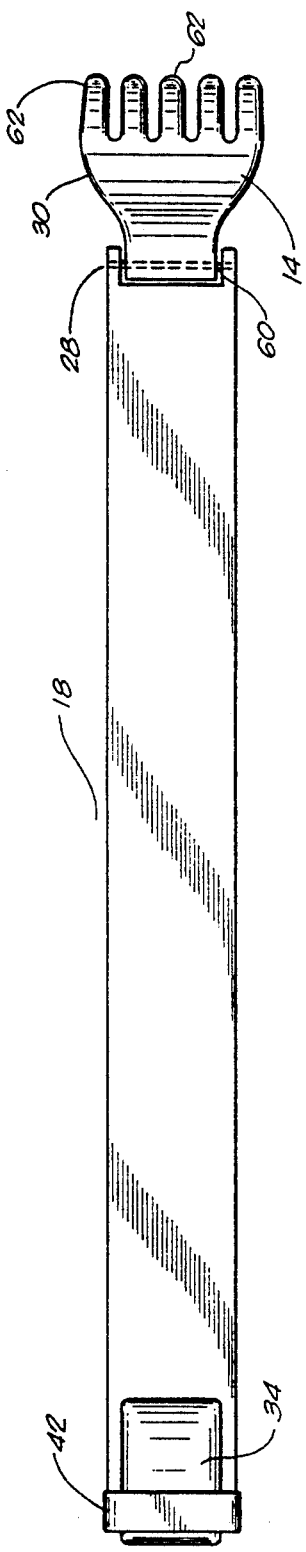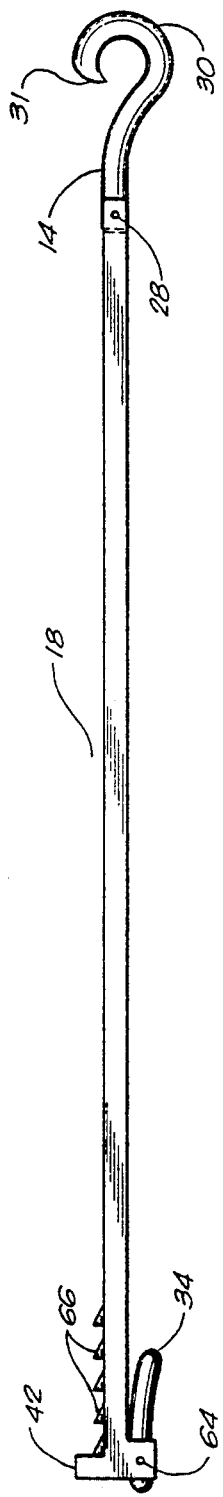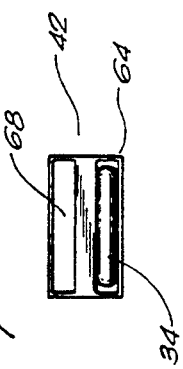

BRACELET RETRACTOR ASSEMBLY

TECHNICAL FIELD

The present invention relates to retractor instruments in general. More particularly, the present invention relates to surgical instruments used for maintaining an incision in an open position.

BACKGROUND ART

Two kinds of retractors are presently used in surgery: hand-held retractors and self-locking tongs. The hand-held retractors are simply a pair of hooks which are inserted at the desired positions under the edge of a cut or wound and held by a nurse or assistant while the surgeon operates. Aside from the additional person required to hold them, such retractors only hold the cut open at two points, unless, of course, additional people and retractors are employed.

Self-locking tong retractors, while not requiring additional people, hold the cut open at only two opposing points. The tong retractors have hooks at the tong ends which are inserted under the cut edge. The ends of the tongs are then spread apart, thereby opening the cut. The tong hinge is fitted with a self-locking ratchet or spring mechanism to hold the wound open. One disadvantage of tong retractors is that it is easy to apply excessive stress to the skin or tissue exposed by the cut with them. Another important disadvantage is the excessive bulk of such devices in the surgical field.

This problem is particularly important with virtually all retractors employed in limb surgery. When the retractors must be used so as to separate the incision, such retractors are often in an awkward and cumbersome position. The position of the retractor can often adversely affect the surgical procedure and creates an obstruction to the observation and viewing of the incision. If persons are employed for the purpose of maintaining the open incision, then this further impedes the surgical process.

In the past, however, various U.S. Patents have been issued with respect to retractor instruments for the exposing of a surgical incision.

U.S. Pat. No. 3,762,401, issued Oct. 2, 1973 to J. W. Tupper shows a surgical retractor for use in hand surgery. This retractor includes a paddle-shaped pallet with notches around the periphery on which the hand is placed, wound-side up. Elastic bands are provided for holding the fingers in place on the pallet. At least one flexible ball-and-link chain with a hook at one end is hooked over the edge of the wound and is fastened to a pallet edge at a predetermined point along its length. An arrangement of such hooks thereby holds the wound open.

U.S. Pat. No. Re. 32,021 also shows a surgical retractor which has a frame conformed to fit the surface contour of the portion of the body to be operated on. A stay is provided which includes an elastic member and suitable tissue holding means. The frame has a plurality of notches spaced around its periphery. The elastic member of the stay is adapted to be inserted into one of the notches and held in place by friction so as to retract the tissue.

U.S. Pat. No. 2,695,607, issued on Nov. 30, 1954 to Hipps et al shows a bone retractor formed of two members which has an offset and a curved portion. This offset portion is adapted so as to engage the underside of a bone. The members extend through the incision to the underside of the bone. A chain engages notches formed on the member. This chain is adapted so as to extend around the periphery of the limb for the purpose of retaining the members in an outward position.

U.S. Pat. No. 2,612,891, issued on Oct. 7, 1952, to M. C. Smith, describes an adjustable support for finger surgery. In particular, a pair of retractor members are fastened within binding posts. By locking a thumb screw in position, the retractors are maintained in an outward position.

Soviet Patent No. 1360-706-A discloses a wound dilator in which a rod is bent along a radius and is equipped with a tubular guide bent along the same radius. A threaded end with a slit is provided on the tubular guide. A fastener, in the form of a nut with an inner cone, is set on the threaded end of the guide. A hinge mechanism is provided so as to allow the wound dilator to engage the edges of the incision.

It is an object of the present invention to provide a retractor instrument which is suitable for maintaining a surgical incision in an open position.

It is another object of the present invention to provide a surgical retractor which does not impede, interfere with, or obstruct the surgical field.

It is another object of the present invention to provide a surgical retractor which is adjustable in a position distal from the incision.

It is still a further object of the present invention to provide a surgical retractor which distributes the retracting force against a large area of the incision.

These and other objects and advantages of the present invention will become apparent from a reading of the attached specification and appended claims.

SUMMARY OF THE INVENTION

The present invention is a retractor instrument that comprises a first tissue holder for grasping an edge of a surgical incision, a second tissue holder for grasping another edge of the surgical incision, a band extending from the first tissue holder to the second tissue holder in a generally circular configuration, and an adjuster connected to the band for acting on the band so as to vary a distance between the first and second tissue holders.

The band includes a first band member which is connected to the first tissue holder and a second band member which is connected to the second tissue holder. The first band member has a plurality of grooves formed along a surface of the first band member. The adjuster includes a clamp which is fastened to the second band member and has means thereon for engaging the grooves of the first band member. The first band member has a slot formed at one end so as to extend around the second band member. Similarly, the second band member has a slide area formed on one end such that the first band member extends therethrough. The clamp is positioned in proximity to the slide area. The clamp is fastened to an exterior surface of the second band member and is movable between a first groove-engaging position and a second free position. The first groove-engaging position is suitable for fixing a position of the first band member with respect to the second band member. The clamp includes a plurality of teeth which extend towards the grooves and have a shape corresponding to the shape of the grooves.

The first tissue holder is a rake member having a plurality of prongs extending therefrom. The rake member is pivotally connected to an end of the band such that it longitudinally extends outwardly and generally parallel to the longitudinal axis of the band. The prongs have a sharp tissue-engaging end. The second tissue holder is also a rake member which has a plurality of prongs extending therefrom. The second rake member is pivotally connected to another end of the band such that it longitudinally extends outwardly and generally parallel to the longitudinal axis of band member 16, as is shown in FIG. 2. The second rake member also has sharp prongs at one end.

The circular configuration of the band has a diameter suitable for extending around a human limb.

The first tissue holder, in an alternative embodiment, includes a first rod received within a first end of the band and a first rake member slidably connected to the first rod. The rake member includes suitable means for affixing a position of the rake member with respect to the rod. A second rake member may also be slidably connected to the rod and includes suitable means for affixing a position with respect to the rod. The second tissue holder includes a second rod which is received within a second end of the band and extends generally parallel to the first rod. A rake member is fastened to the second rod and includes suitable means for affixing a position of the rake member with respect to the second rod.

BRIEF DESCRIPTION OF THE DRAWINGS

FIG. 2 is a top view of the first band member in an extended position.

FIG. 3 is a cross-sectional view of the first band member of the present invention.

FIG. 4 is a right side end view of the first band member of the present invention.

FIG. 5 is a top view of the second band member of the present invention.

FIG. 6 is a view, in side elevation, of the second band member of the present invention.

FIG. 7 is a left side end view of the second band member of the present invention.

DETAILED DESCRIPTION OF THE INVENTION

Figure 1:
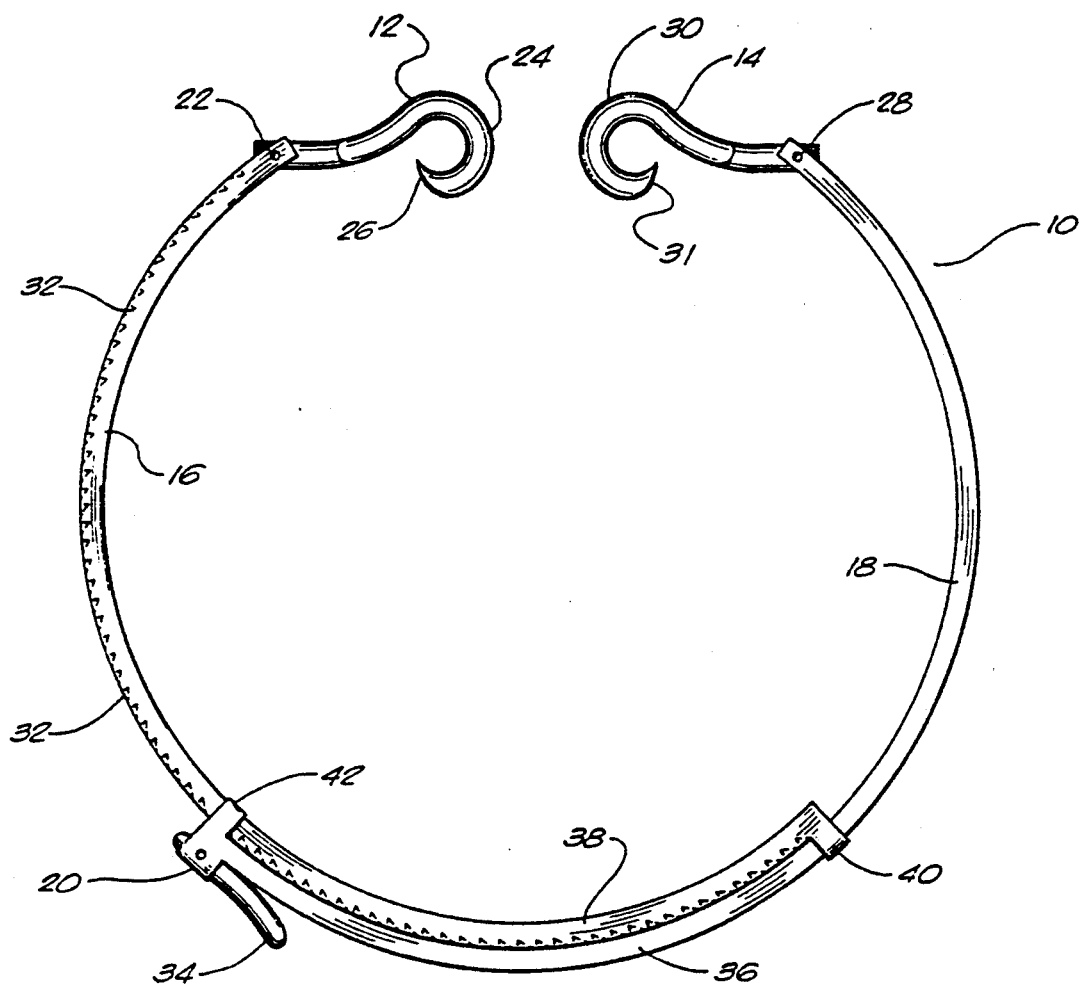
FIG. 1 is a view in side elevation of the bracelet retractor in accordance with the preferred embodiment of the present invention.

Referring to FIG. 1, there is shown at 10 the surgical bracelet retractor in accordance with the preferred embodiment of the present invention. The surgical retractor 10 includes a first tissue holder 12, a second tissue holder 14, a first elongated band member 16, a second elongated band member 18, and an adjuster 20. Each of these elements cooperates so as to provide a surgical retractor suitable for opening an incision on a human limb. The configuration of the first band member 16 and the second band member 18 is generally circular so as to extend around the limb away from the incision.

Initially, the first tissue holder 12 is pivotally connected at 22 to an end of the first band member 16. The pivotal relationship between the first tissue holder 12 and the first band 16 facilitates the use of the present invention around a human limb. The use of the pivotal connection 22 allows for automatic adjustment between the tissue holder 12 and the first band member 16 so as to conform to the contour of the human limb. As will be described hereinafter, the first tissue holder 12 includes a first rake member 24 which has a plurality of prongs 26 extending inwardly therefrom. The prongs have a sharp tissue-engaging end. In conventional use, the prongs 26 of rake member 24 will engage an edge of the surgical incision. The forces imparted by the circular band will cause the rake member 24 to retain the incision in an open position.

The second tissue holder 14 is pivotally connected at 28 to an end of the second band member 18. As before, the pivotal connection between the tissue holder 14 and the second band member 18 allows for the self-adjustment to the contours of the human limb. The second tissue holder 14 also, includes a rake member 30 having inwardly extending prongs 31. The tissue holders 12 and 14 are configured so as to grasp opposite sides of the surgical incision. It can be seen that the movement of one of the tissue holders with respect to another of the tissue holders serves to open the incision by creating a pulling force on the rake members 24 and 30, along with their respective prongs 26 and 31.

The first band member 16, in combination with the second band member 18, forms a generally circular configuration between the pivotal connections 22 and 28 associated with the first tissue holder 12 and the second tissue holder 14, respectively. The adjustment means 20 is configured so as to allow for the movement of the first band member 16 with respect to the second band member 18.

It can be seen that the first band member 16 has a plurality of grooves 32 extending along an exterior surface of the first band member 16. Each of the grooves 32 is indented into the surface so as to create a ratchet-like appearance. The adjuster 20 includes a clamp 34 which is attached to the second band member 18.

The second band member 18 includes an overlapping portion 36 which extends over an underlapping portion 38 of the first band member 16. The first band member 16 has a slot 40 formed at one end so as to extend around the perimeter of the second band member 18. Similarly, the second band member 18 includes a slide area 42 which extends around the perimeter of the first band member 16. The clamp 34 is placed in proximity to the slide area 42.

The clamp 34 is pivotally mounted on an exterior surface of the second band member 18 at the end of the overlapping portion 36. The clamp 34 is movable between a first groove-engaging position (shown in FIG. 1) and a second free position. When the clamp 34 is in the position shown in FIG. 1, the clamp 34 serves to fix the position of the first band member 16 with respect to the second band member 18. The manipulation of the clamp 34, along with the sliding relationship between the first and second band members, allows for the proper adjustment of the distance between the first tissue holder 12 and the second tissue holder 14. Specifically, the clamp 34 includes a plurality of teeth which extend toward the grooves 32. The teeth have a shape corresponding to the shape of the grooves 32.

Typically, the tissue holders 12 and 14, along with the first band member 16 and the second band member 18, are made of a flexible steel material. The diameter of the circular configuration of the retractor 10 should be suitable for extending around the circumference of a human limb. The flexibility of the band members 16 and 18 facilitates the ability of the retractor 10 to conform to the shape of the human limb.

FIG. 2 illustrates the configuration of the first band member 16 as isolated from the second band member 18. The first band member 16 appears as a strip of a flexible material, such as a strip of steel. In general, the first band member 16 has an extended rectangular configuration. The slot 40 is formed at one end of the band member 16. The tissue holder 12 is pivotally connected at 22 to the other end of the band member 16. A plurality of grooves 32 are shown as extending transversely across the band member 16 along the length of the band member 16 at regular intervals. In FIG. 2, for the purposes of clarity, not all of the grooves 32 are illustrated. Within the concept of the present invention, a small number of grooves 32 may be included (as shown in FIG. 2), or the grooves can extend for the entire length of the first band member 16. The configuration of the grooves, the size of the grooves, and the number of grooves, is adaptable to fit the particular use to which the retractor 10 is intended.

The tissue holder 12 is pivotally connected around rod 50 at the end of band member 16 opposite slot 40. The tissue holder 12 includes a rake 24 which longitudinally extends outwardly and generally parallel to the longitudinal axis of band member 16, as is shown in FIG. 2. It can be seen that the rake 24 has a plurality of fingers 52 extending outwardly therefrom. Fingers 52 serve to distribute the retracting force over a wide area.

FIG. 3 is a cross-sectional view of the first band member 16. It can be seen that the first band member 16 has a plurality of ratchet-shaped grooves 32 extending along the entire length of the band member 16. The tissue holder 12 is pivotally connected at 22 to the band member 16. The sharp prongs 26 extend inwardly from the rake member 24 of tissue holder 12. Slot 40 is shown at the opposite end of the first band member 16.

FIG. 4 shows the slot 40. Slot 40 includes a solid area 54 and an open slide area 56. Slide area 56 is suitable for receipt of the perimeter of the second band member 18. Slide area 56 should be suitable so as to allow the second band member to slide easily with respect to the first band member 16. The slot 40 at the end of the first band member 16 assures that the first band member 16 conforms, in a circular configuration, with the inner surface of the second band member 18.

FIG. 5 is an isolated view of the second band member 18. It can be seen that the second band member 18 has a generally extended rectangular shape. The second band member 18 has a slide area 42 and a clamp 34 positioned at one end and the tissue holder 14 positioned at the other end. The slide area 42 extends across the width of a band member 18. The clamp 34 is pivotally received within the slide area 42 so as to be movable between a first position and a second position. The tissue holder 14 has a similar configuration to the tissue holder 12, as shown in FIGURE 2. Specifically, the tissue holder 14 is pivotally connected at 28 to the end of the band 18 A rod 60 is received within the end of band 18 and extends through the tissue holder 14. Tissue holder 14 includes a rake portion 30 having a plurality of fingers 62 extending outwardly therefrom. The width of the second band member 18 should generally correspond to the width of the first band member 16.

FIG. 6 shows a side view of the second band member 18. The second band member 18 is shown as having the slide area 42 formed at one end. The clamp 34 is pivotally connected at 64 to the slide area 42. A plurality of teeth 66 are connected to the clamp 34 so as to be movable between a first groove-engaging position and a second free position. When the clamp 34 is in the position illustrated in FIG. 6, the teeth 66 are suitable for engaging the grooves 32 on the first band member 16. This serves to lock the second band member into a proper position with respect to the first band member 16. It can be seen at the other end of the second band member 18 that the tissue holder 14 is pivotally connected at 28 to the end of band member 18 in such a fashion that the rake portion 30 longitudinally extends outwardly and generally parallel to the longitudinal axis of band member 18. The rake portion 30 includes prongs 31 so as to properly engage the tissue of the surgical incision.

FIG. 7 shows an end view of the slide area 42. It can be seen that the slide area 42 includes the pivotal connection 64 of clamp 34. The slide area 42 also includes a slotted opening 68 suitable for receipt of the perimeter of the first band member 16. In normal use, the slotted opening 68 of the slide area 42 will receive the first band member 16 so as to allow the first and second band members to conform in a circular configuration.

Figure 8:
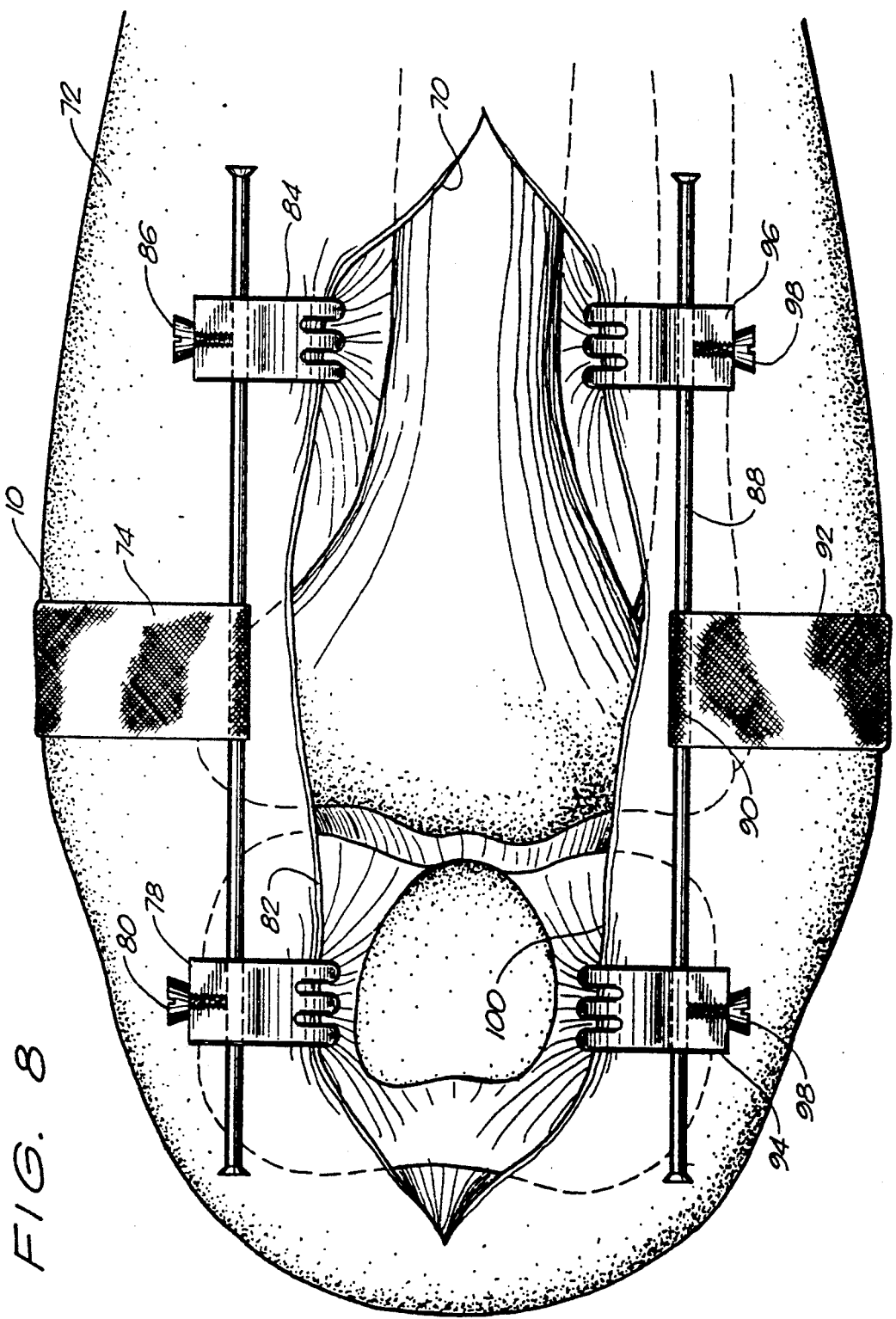
FIG. 8 is a top view of the bracelet retractor, of an alternative embodiment of the present invention, as used in conjunction with a surgical incision.

FIG. 8 illustrates the use of the present invention 10 on a surgical incision 70. In particular, the surgical incision 70 is placed on a human limb 72. The retractor instrument 10 of the present invention is shown as in an alternative embodiment. It can be seen that the retractor 10 of the present invention is used to retain a surgical incision 70 in a proper open position so as to expose the interior of the limb 72.

The retractor 10 is shown as extending around the periphery of the limb 72 away from the incision 70. As a result, there are no apparatus or other instruments to interfere with or obstruct the surgical field.

In the embodiment shown in FIG. 8, the first band member 74 extends around one side of the limb 72 and terminates adjacent to the surgical incision 70. A rod 76 is received within the end of the first band member 74. Rod 76 has a suitable length corresponding to the length of the incision. The rod 76 extends outwardly generally perpendicular to the band 10. A first rake member 78 is slidably connected to the rod 76. The first rake member 78 includes a suitable mechanism 80 for the purpose of fixing a position of the first rake member 78 with respect to rod 76. As shown in FIG. 8, the mechanism 80 is a pin or threaded member which can be rotated so as to abut the surface of the rod 76. By tightening the head of the threaded member 80, suitable engagement forces can be imparted to the surface of rod 76. The rake member 78 has its prongs engaging the inner surface of the edge 82 of incision 70.

A second rake member 84 is positioned on an opposite area of the rod 76. The second rake member 84 slidably engages the rod 76. The second rake member 84 also includes a mechanism 86 for fixing the position of the second rake member 84 with respect to rod 76. The mechanism 86 can have a configuration similar to that of mechanism 80 on the first rake member 78. In the configuration shown in FIG. 8, the rake members 78 and 84 can slide with respect to the rod 76 so as to be in position for properly retracting the incision 70. The second rake member 84 includes prongs for engaging the edge 82 of the incision 70.

A second rod 88 is received within a second end 90 of the second band member 92 of retractor 10. The second rod is arranged so as to be in a generally parallel relationship with the first rod 76. A first rake member 94 is slidably fastened to the rod 88. Similarly, a second rake member 96 is also slidably fastened to the rod 88. Each of the rake members 94 and 96 include mechanisms 98 for affixing the rake members in a position on the rod 88. The rake members 94 and 96 include suitable prongs for engaging the edge 100 of surgical incision 70.

After the surgical incision 70 is made, the prongs may be inserted into the flesh so as to properly secure the rake members to the flesh. A force can be applied to the first band member 74 and/or the second band member 92 so as to cause the rods 76 and 88 to separate, thereby opening the incision 70. When a suitable separation of the edges 82 and 100 has occurred, the clamp 34 can be properly closed so as to lock the position of the rake members and to fix the opening of the incision.

The present invention is of great benefit for those carrying out surgical procedures on human limbs. Most importantly, this "bracelet" style of retractor provides the necessary retracting forces without interfering with the surgical field. As such, proper surgical procedures can be carried out without interference from the retractor instruments or from the hands of assistants. After the surgical procedure is over, the retractor can be easily removed by opening the clamp so as to allow each of the band members to slide with respect to the other band member.

The foregoing disclosure and description of the invention is illustrative and explanatory thereof. Various changes in the details of the illustrated construction may be made within the scope of the appended claims without departing from the true spirit of the invention. The present invention should only be limited by the following claims and their legal equivalents.

I claim:

1. A retractor instrument comprising:
  a first tissue holding means for grasping an edge of a surgical incision;
  a second tissue holding means for grasping another edge of the surgical incision;
  a flexible steel elongated band extending from said first tissue holding means to said second tissue holding means, said band having a generally circular configuration, said first tissue holding means comprising a first rake member having a plurality of prongs extending therefrom, said first rake member being pivotally connected to an end of said band such that said first rake member longitudinally extends outwardly and generally parallel to the longitudinal axis of said band, said second tissue holding means comprising a second rake member having a plurality of prongs extending therefrom, said a second rake member being pivotally connected to another end of said band such that said second rake member longitudinally extends outwardly and generally parallel to the longitudinal axis of said band, each of said plurality of prongs of said first and second rake members having a sharp tissue-engaging end; and
  adjustment means directly connected to said band, said adjustment means for acting on said band so as to vary a distance between said first and second tissue holding means.

2. The retractor instrument of claim 1, said band comprising:
  a first band member connected to said first tissue holding means; and
  a second band member connected to second tissue holding means, said adjustment means for moving said first band member relative to said second band member.

3. The retractor instrument of claim 2, said first band member having a plurality of grooves formed along a surface of said first band member, said adjustment means comprising:
  a clamp fastened to said second band member, said clamp having means thereon for engaging said grooves of said first band member.

4. The retractor instrument of claim 3, said first band member having a slot formed at one end, said slot extending around said second band member.

5. The retractor instrument of claim 4, said second band member having a slide area formed at one end, said first band member extending through said slide area, said clamp positioned in proximity to said slide area.

6. The retractor instrument of claim 5, said clamp fastened on an exterior surface of said second band member, said clamp movable between a first groove-engaging position and a second free position, said first position for fixing a position of said first band member with respect to said second band member.

7. The retractor instrument of claim 3, said means for engaging said grooves comprising:
  a plurality of teeth extending toward said grooves, said teeth having a shape corresponding to a shape of said grooves.

8. The retractor instrument of claim 1, said circular configuration of said band having a diameter suitable for extending around a human limb.

9. A retractor for opening a surgical incision on a human limb comprising:
  a first tissue holding means for grasping an edge of the surgical incision;
  a second tissue holding means for grasping another edge of the surgical incision;
  a first band member connected to said first tissue holding means;
  a second band member connected to said second tissue holding means, said first band member having a portion in overlapping relationship with said second band member, said first and second band members having a configuration for extending around the human limb away from the incision, said first tissue holding means comprising a first rake member having a plurality of prongs extending therefrom, said first rake member being pivotally connected to an end of said first band member, said prongs having a sharp tissue-engaging end, said second tissue holding means comprising a second rake member having a plurality of prongs extending therefrom, said second rake member being pivotally connected to an end of said second band member, each of said prongs having a sharp tissue-engaging end; and
  adjustment means connected to said first band member and to said second band member, said adjustment means for varying a distance between said first tissue holding means and said second tissue holding means.

10. The retractor of claim 9, said first and second band members comprised of a flexible steel material.

11. The retractor of claim 9, said first band member having a plurality of grooves formed along a surface of said first band member, said adjustment means comprising:

a clamp fastened to said second band member, said clamp having means thereon for engaging said grooves of said first band member.

12. The retractor of claim 11 said first band member having a slot formed at one end, said slot extending around said second band member, said second band member having a slide area formed at one end, said first band member extending through said slide area, said clamp positioned in proximity to said slide area.

13. The retractor of claim 12, said clamp fastened to an exterior surface of said second band member, said clamp movable between a first groove-engaging position and a second free position, said first position for fixing a position of said first band member with respect to said second band member.

* * * * *